(12) United States Patent
Rabito et al.

(10) Patent No.: US 11,904,120 B2
(45) Date of Patent: *Feb. 20, 2024

(54) LEFT ATRIAL APPENDAGE STASIS REDUCTION

(71) Applicant: NXT Biomedical, LLC, Irvine, CA (US)

(72) Inventors: Glen Rabito, Irvine, CA (US); Joseph Passman, Irvine, CA (US); Robert C. Taft, Irvine, CA (US); Stanton J. Rowe, Irvine, CA (US); Robert S. Schwartz, Irvine, CA (US); Alexander Siegel, Irvine, CA (US)

(73) Assignee: NXT Biomedical, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/069,025

(22) Filed: Dec. 20, 2022

(65) Prior Publication Data

US 2023/0129101 A1  Apr. 27, 2023

Related U.S. Application Data

(63) Continuation of application No. 17/662,413, filed on May 6, 2022, now Pat. No. 11,559,672, which is a
(Continued)

(51) Int. Cl.
*A61M 27/00* (2006.01)
*A61M 60/165* (2021.01)
(Continued)

(52) U.S. Cl.
CPC ....... *A61M 27/002* (2013.01); *A61B 17/0057* (2013.01); *A61F 2/2487* (2013.01);
(Continued)

(58) Field of Classification Search
CPC .............. A61M 27/002; A61M 27/006; A61M 2205/75; A61M 2206/20;
(Continued)

(56) References Cited

U.S. PATENT DOCUMENTS

| 4,995,857 A | 2/1991 | Arnold |
| 5,879,375 A | 3/1999 | Larson, Jr. et al. |

(Continued)

FOREIGN PATENT DOCUMENTS

WO   WO 2021/025905 A1   2/2021

OTHER PUBLICATIONS

European Patent Office, Partial Supplementary Extended European Search Report dated Oct. 10, 2022 in European Patent Application No. 20752451.3, 12 pages.
(Continued)

*Primary Examiner* — Philip R Wiest
(74) *Attorney, Agent, or Firm* — Inskeep IP Group, Inc.

(57) ABSTRACT

Methods and devices that prevent stasis in the LAA by either increasing the flow through the LAA or by closing off or sealing the LAA. Increasing the flow is accomplished through shunts, flow diverters, agitators, or by increasing the size of the ostium. Closing off the LAA is accomplished using seals or by cinching the LAA.

18 Claims, 14 Drawing Sheets

Related U.S. Application Data continuation of application No. 17/424,840, filed as application No. PCT/US2020/017102 on Feb. 6, 2020, now Pat. No. 11,369,780.

(60) Provisional application No. 62/906,001, filed on Sep. 25, 2019, provisional application No. 62/881,239, filed on Jul. 31, 2019, provisional application No. 62/845,528, filed on May 9, 2019, provisional application No. 62/835,434, filed on Apr. 17, 2019, provisional application No. 62/803,337, filed on Feb. 8, 2019.

(51) Int. Cl.
*A61M 60/216* (2021.01)
*A61B 17/00* (2006.01)
*A61F 2/24* (2006.01)
*A61F 2/82* (2013.01)
*A61M 60/161* (2021.01)
*A61M 60/289* (2021.01)
*A61M 60/861* (2021.01)

(52) U.S. Cl.
CPC .............. *A61F 2/82* (2013.01); *A61M 60/161* (2021.01); *A61M 60/165* (2021.01); *A61M 60/216* (2021.01); *A61M 60/289* (2021.01); *A61M 60/861* (2021.01); *A61B 2017/00632* (2013.01); *A61M 2205/75* (2013.01); *A61M 2206/20* (2013.01); *A61M 2210/125* (2013.01)

(58) Field of Classification Search
CPC ......... A61M 2210/125; A61B 17/0057; A61B 2017/00632; A61F 2/2487; A61F 2/82
See application file for complete search history.

(56) References Cited

U.S. PATENT DOCUMENTS

| | | | |
|---|---|---|---|
| 7,674,238 | B2 | 3/2010 | Weber et al. |
| 7,806,846 | B2* | 10/2010 | Chanduszko ......... A61F 2/2493 |
| | | | 604/8 |
| 8,597,225 | B2 | 12/2013 | Kapadia |
| 9,089,414 | B2 | 7/2015 | Zimmerman |
| 9,492,623 | B2 | 11/2016 | Kapadia et al. |
| 10,137,229 | B2 | 11/2018 | Asirvatham et al. |
| 11,559,672 | B2* | 1/2023 | Rabito ...................... A61F 2/07 |
| 2002/0077596 | A1 | 6/2002 | McKenzie et al. |
| 2005/0070993 | A1 | 3/2005 | Boekstegers et al. |
| 2005/0154250 | A1 | 7/2005 | Aboul-Hosn et al. |
| 2005/0234540 | A1* | 10/2005 | Peavey ............ A61B 17/12172 |
| | | | 623/1.42 |
| 2012/0022427 | A1* | 1/2012 | Kapadia ............. A61B 17/0057 |
| | | | 604/8 |
| 2014/0228733 | A1* | 8/2014 | Martinez ................ A61B 17/11 |
| | | | 604/8 |
| 2015/0238728 | A1 | 8/2015 | Wach et al. |
| 2015/0328026 | A1* | 11/2015 | Zimmerman ........... A61F 2/844 |
| | | | 623/1.13 |
| 2018/0078394 | A1 | 3/2018 | Zimmerman et al. |
| 2018/0206830 | A1 | 7/2018 | Khairkhahan et al. |

OTHER PUBLICATIONS

WIPO, U.S. International Search Authority, International Search Report and Written Opinion dated Jun. 26, 2020 in International Patent Application No. PCT/US2020/017102, 10 pages.

European Patent Office, Supplementary European Search Report dated Feb. 3, 2023 in European Patent Application No. 20752451.3, 7 pages.

\* cited by examiner

LEFT ATRIAL APPENDAGE STASIS REDUCTION

RELATED APPLICATIONS

This application is a continuation of and claims benefit of and priority to U.S. application Ser. No. 17/662,413 filed May 6, 2022 entitled Left Atrial Appendage Stasis Reduction, which is a continuation of and claims benefit and priority to U.S. application Ser. No. 17/424,840 filed Jul. 21, 2021, entitled Left Atrial Appendage Stasis Reduction (now U.S. Pat. No. 11,369,780 issued Jun. 28, 2022), which is the U.S. National Phase of and claims priority to International Patent Application No. PCT/US2020/017102, International Filing Date Feb. 6, 2020, entitled Left Atrial Appendage Stasis Reduction, which claims benefit of and priority to U.S. Provisional Patent Application Ser. No. 62/803,337 filed Feb. 8, 2019 entitled LAA Stasis Reduction; U.S. Provisional Patent Application Ser. No. 62/835,434 filed Apr. 17, 2019 entitled LAA Stasis Reduction; U.S. Provisional Patent Application Ser. No. 62/845,528 filed May 9, 2019 entitled LAA Stasis Reduction; U.S. Provisional Patent Application Ser. No. 62/881,239 filed Jul. 31, 2019 entitled Coronary Artery-LAA Shunt; and U.S. Provisional Patent Application Ser. No. 62/906,001 filed Sep. 25, 2019 entitled LAA Flow Augmentation, all of which are hereby incorporated herein by reference in their entireties.

BACKGROUND OF THE INVENTION

The left atrial appendage, or "LAA" as it will be referred to herein, is a structure that gives rise to stagnant blood flow and thrombus formation, especially in patients suffering from atrial fibrillation. It has been approximated that 90% of blood clots developed in atrial fibrillation cases are formed in the LAA. As the function of the LAA is thought to be mainly embryonic, one solution is to surgically remove the atrial appendage, typically concomitant mitral valve surgery. However, surgery is always associated with risks due to infection, bleeding, incomplete ablation, etc.

Efforts have been directed lately toward various devices and techniques to percutaneously ablate, close or occlude the LAA. Examples of such devices include the WATCHMAN device developed by Atritech Inc., of Plymouth, Minn. and the PLAATO device developed by Appriva Medical, Inc., of Sunnyvale, Calif. Occluding the LAA is undesirable for a variety of reasons, for example, because the LAA is a source of important hormones, and because the geometry of the LAA varies from person to person, making occlusion of the oval-shaped ostium with an implant difficult. Also, known occlusion devices typically are mounted or secured to tissue surrounding the LAA. Since the tissue surrounding the LAA is relatively thin, implanting such an occlusion device can increase the risk of rupture and pericardial effusion. Moreover, all such devices leave a large, prosthetic surface at the ostium of the LAA, which can be thrombogenic, cause irritation, or inflammation. Additionally, it is believed that the LAA acts as a compliance chamber and helps to regulate blood pressure in the left atrium. Hence, it is desirable to maintain the flow of blood through the LAA.

There is thus a need for a method and device useable to prevent blood from stagnating in the LAA, while having a compliance that does not interfere with normal blood flow through the left atrium, and does not result in pericardial effusion, embolization, and a loss of device integrity. There is also a need for a device that permits ostial ablation and presents an immediate and long-term tissue interface to the left atrial blood.

More specifically, there is a need for a method and device for establishing flow into the apex of the left atrial appendage, an intervention eliminating blood stasis and thus eliminating or limiting the formation of thrombus, or other stagnant particles which can embolize to the systemic circulation and cause stroke or other systemic emboli.

OBJECTS AND SUMMARY OF THE INVENTION

The embodiments of the invention are directed to preventing stagnation and thrombogenesis in the LAA. The many embodiments of devices and methods shown and described herein can be divided into two broad categories: 1) Increasing blood flow through the LAA, and 2) Sealing the LAA.

The first category involves devices and methods used to increase blood flow through the LAA. By increasing the blood flow through the LAA, the risk of embolic materials developing is greatly reduced because stagnated blood is no longer present in the LAA.

Some of the embodiments directed toward increasing blood flow through the LAA involve shunts or diverters that direct blood into the LAA that would normally bypass the LAA. In one representative embodiment, a shunt is placed directing flow from the pulmonary artery to the LAA. The shunt may be used in combination with a filter to prevent any embolic material present in the LAA from entering the pulmonary artery.

Another embodiment involves the placement of a shunt that directs flow from the left ventricle to the LAA. The left ventricle pressures are high enough, relative to the LAA, that retrograde or regurgitant flow could be established through a shunt between the left ventricle and the LAA. After leaving the shunt, the blood flow washes out the LAA and returns to the left atrium where it rejoins normal blood flow through the heart. Due to the high pressures in the left ventricle, only a small amount of blood flow would be necessary, thereby minimizing the size of the shunt.

Another embodiment involves the placing of a shunt between the LAA and the coronary sinus to increase flow through the LAA and reduce stasis.

Yet another embodiment of the invention places a shunt between a coronary artery and the LAA to increase flow through the LAA and reduce stasis.

Still another embodiment of the invention involves placing a covered device to shunt blood between the LAA and the right atrium (RA) through the septum to increase flow through the LAA and reduce stasis.

Other embodiments of the invention involve directing flow from the pulmonary vein (PV) to the LAA. Some of these embodiments use a flow diverter that is anchored to the left lateral ridge LLR (or coumadin ridge) of the left atrium and causes some of the blood to be diverted into the neighboring LAA. Other embodiments include placing a shunt in the pulmonary vein at a location upstream of the LLR, leading to an interior location of the LAA. In order to ensure the flow would be diverted, a flow restrictor may be placed near the LLR that builds pressure in the PV to ensure flow is established through the shunt. Alternatively, flow from the LAA into the PV may be established without a restrictor due to the lower pressure created by the flow through the PV.

Yet another embodiment that increases flow through the LAA involves the placement of a left atrial sail to deflect, direct or divert flow into the LAA from the PV. One embodiment anchors the sail to the top of the LA near the LAA ostium. One embodiment provides a sail constructed of a fabric, ePTFE, polymer or tissue. In at least one embodiment, the sail has a suture tightening mechanism. In yet another embodiment, the sail has an anchor within the LAA ostium. In at least another embodiment, the sail has an anchor or anchors at the interatrial septum. In at least one embodiment, the sail includes a compression spring used to angle the device. The sail may be placed to bisect the LA with anchors at the annulus and the top of the LA. One embodiment provides a sail with anchors placed at the annulus, with a kickstand or shaped wire element that achieves the desired angle of the device to redirect flow towards the LAA ostium.

Still other embodiments of the invention that establish blood flow through the LAA involve implants that are external to the LAA but use the walls of the LAA to act as a pump. In one example, plates are placed on opposite sides of the LAA, external to the LAA, and connected through the LAA with a connector. A driving mechanism, either active or passive, is used to change the distance between the two plates, such that the plates turn the LAA into a bellows that drives blood into and out of the LAA.

Another embodiment increases flow through the LAA by increasing the size of the LAA ostium and the cavity of the LAA using an expandable stent.

The second category of devices and methods of the invention are directed to reducing flow through the LAA either by reducing the size of the LAA without placing an occlusive device within the LAA, or by blocking the ostium of the LAA. One such embodiment involves a transseptal LAA external cinch closure procedure and device. A cinch loop is deployed in the pericardial space and used to collapse or tie off the LAA near its opening.

Another closure concept also involves a pericardial cinch but uses a suture lock accessible from within the LA.

Yet another embodiment of a closure device is a modification of the aforementioned cinch concepts in which multiple helical loops in the form of a spiral or corkscrew are used to cinch the LAA. This concept may help disperse the forces exerted on the LAA and prevent damage thereto and more complete closure.

One embodiment of a helical closure device and method uses a spiral needle to establish a desired path through and around the LAA. A suture is then passed through the needle and anchored outside of the LAA. The needle is retracted leaving the suture in place, which is then cinched and tied.

One embodiment that blocks the ostium of the LAA provides an LAA closure device that is anchored on the LLR and contains a conforming structure to occlude the LAA ostium. The device could contain a torsional element to apply force to the occlusive element to optimize the seal over the ostium.

The foregoing and other objects, features, and advantages will become more apparent from the following detailed description, which proceeds with reference to the accompanying figures.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
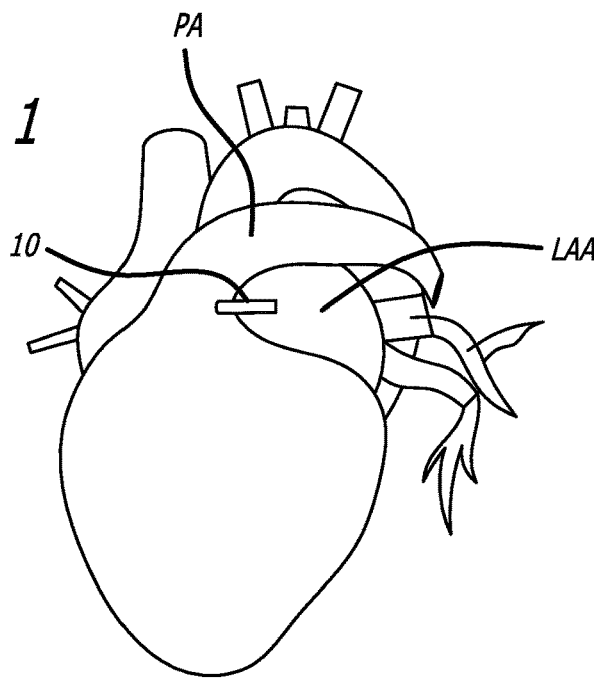
FIG. 1 is a diagram of an embodiment of a shunt placed in the heart according to the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Increasing Blood Flow Through the LAA

Several embodiments of devices and methods for increasing the blood flow through the LAA are shown and described herein. Referring first to FIG. 1, there is shown an embodiment of a shunt 10 connecting the pulmonary artery PA to the LAA. The shunt may be used in combination with a filter, either internal or external to the shunt 10. The flow through the shunt 10 will travel from a higher pressure to a lower pressure, typically from the PA to the LAA. However, during certain points in the cardiac cycle, the pressure in the LAA may be higher than the pressure in the PA. During these points there may be retrograde flow through the shunt 10. Alternatively, a one-way valve could be incorporated into the shunt 10 to prevent retrograde flow from the LAA to the PA.

The shunt 10 is shown in FIG. 1 as a simple tube providing a lumen between the LAA and the PA. One skilled in the art will realize that the diameter and length of the lumen will dictate the degree to which the fluid traveling through the shunt will effectively "wash-out" or maintain circulation within the LAA to prevent stasis. The larger the diameter of the lumen, and the shorter the length of the shunt, the greater the flow through the lumen. However, as an unnatural flow path is being established in the heart, the size of the shunt should be selected to be just large enough to accomplish the prevention of stasis. The optimal size of the shunt will likely be determined by factors unique to each patient, such as heart size, LAA size, blood pressure, thrombogenesis tendencies, cholesterol levels, etc.

Various shunt design embodiments are envisioned for all of the shunt embodiments listed herein. Non-limiting examples include lined braided nitinol stents, stainless steel shunts, polymer shunts, magnet shunts, biodegradable shunts, or non-implantable shunt creation via anastomosis.

Anchoring the shunts may be accomplished with expandable flared ends, radial force, wings, flanges, sutures, magnets, barbs, microanchors, and the like. Anchoring may be further enhanced through the use of external coatings that promote ingrowth and/or synthetic sealing, adhesives, etc.

Implanting the shunts described herein may be accomplished laproscopically, percutaneously using a transcatheter procedure, surgically, transthoracically and the like.

Figure 2:
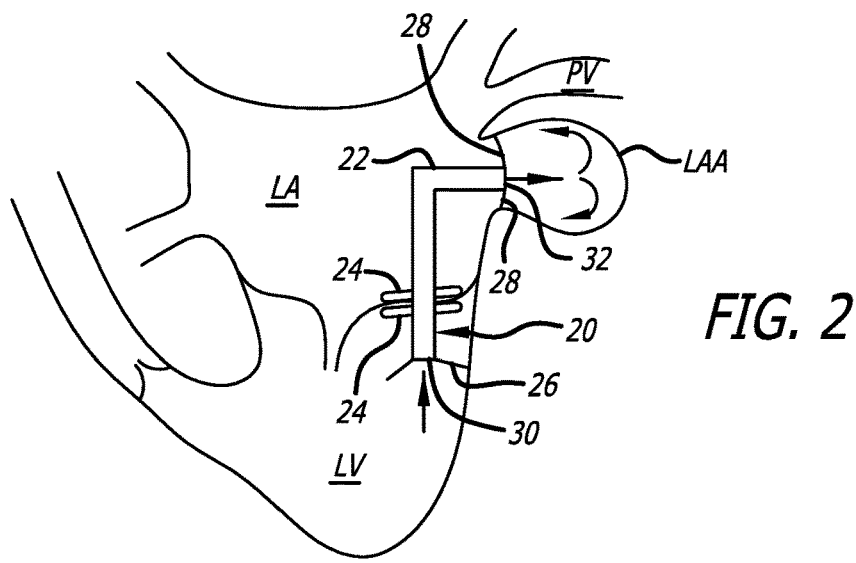
FIG. 2 is a cutaway view of the heart with an embodiment of a shunt placed in the heart according to the invention.

FIG. 2 shows an embodiment of a shunt 20 that directs flow from the left ventricle LV to the LAA. The left ventricle pressures are high enough, relative to the LAA, that retrograde or regurgitant flow could be established between the LV and the LAA. After leaving the shunt 20, the blood flow washes out the LAA and returns to the left atrium where it rejoins normal blood flow through the heart. Due to the high pressures in the left ventricle, only a small amount of blood flow would be necessary, thereby minimizing the size of the shunt.

Figure 3:
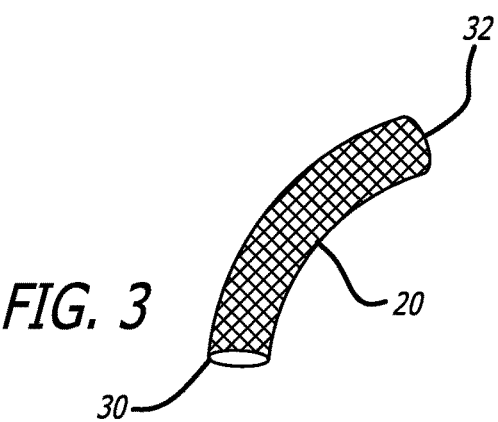
FIG. 3 is a plan view of an embodiment of a shunt of the invention to be placed according to FIG. 2.

The shunt 20 is shown as including an angled bend 22 that directs the flow into the LAA. Though shown as a sharp angle, the shunt 20 may be incorporate a gentle curve or a plurality of curves to direct the flow from the LV to the LAA while minimizing flow resistance that may result from sharp bends. FIG. 3 shows an embodiment of the shunt 20 that uses a braided structure with a gentle bend.

The shunt 20 passes through the sinus of the mitral valve and may be anchored thereto. Like shunt 10, anchoring may be accomplished through the use of flares, flanges, wings, sutures, and the like, however the anchoring features 24 may be located at a midpoint of the shunt 20 where the shunt passes through the mitral valve sinus. Additional anchors 26 and 28 may be included near the ends 30 and 32 to accommodate the high pressures and significant movement generated by the beating heart. These additional anchors 26 and 28 may also be in the form of flares, flanges, wings, sutures, and the like.

It is conceived that this shunt, as well as the other shunt embodiments described herein, may be oriented such that the blood flow into the LAA is directed toward a sidewall of the LAA, as opposed to being directed straight into the LAA, in order to create a vortex within the LAA. A vortex would ensure a complete flushing of the LAA, much like the flushing of a toilet bowl.

Figure 4:
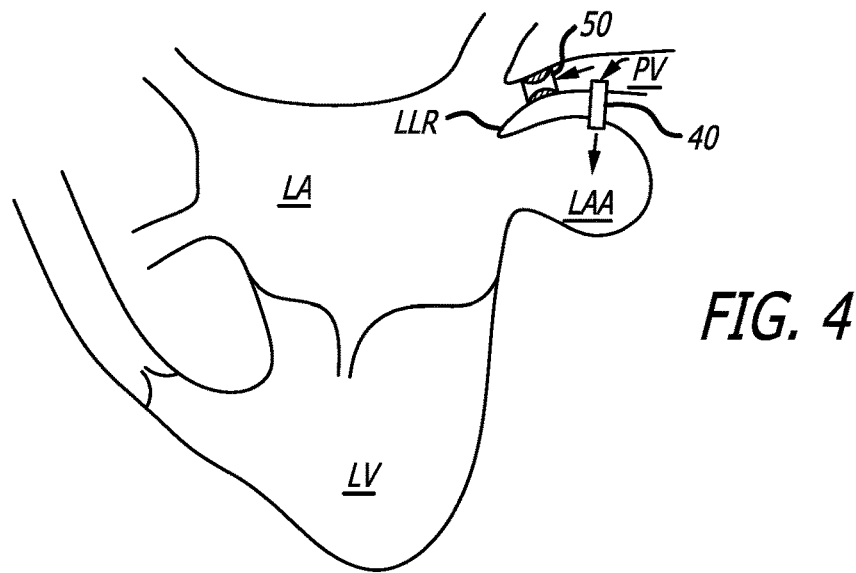
FIG. 4 is a cutaway view of the heart with an embodiment of a shunt placed in the heart according to the invention.

FIG. 4 shows an embodiment of a shunt 40 placed between the pulmonary vein PV and the LAA. The pulmonary vein blood flow will follow the path of least resistance; therefore the majority of the flow will enter the left atrium LA through the PV rather than into the LAA through the shunt. However, if a resistor 50 is added downstream of the shunt 40, closer to the LLR, the resistance to flow is increased and more blood flow will pass through the shunt 40 into the LAA. The resistor 50 could be a stent-like structure or a braided flow inhibitor, for example. Like the other shunt embodiments, the diameter and the length of the stent 40 are selected, along with the size of the resistor 50, to ensure adequate washout of the LAA occurs without overly restricting or disrupting flow through the left side of the heart.

Figure 5:
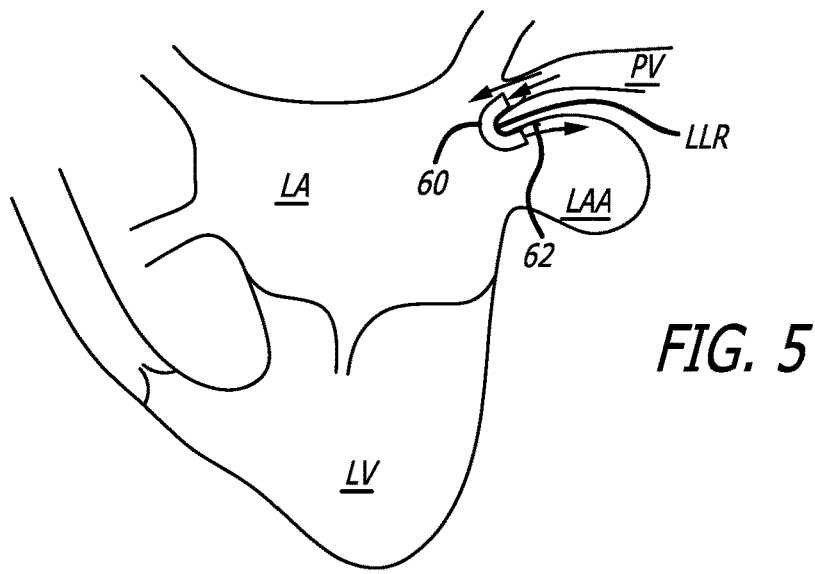
FIG. 5 is a cutaway view of the heart with an embodiment of a shunt placed in the heart according to the invention.

FIG. 5 depicts an embodiment of a flow diverter 60 that redirects a portion of the blood exiting the PV around the left lateral ridge LLR (or coumadin ridge) and into the LAA. The flow diverter 60 is a U-shaped stent or shunt that is anchored to the LLR of the LA. In at least one embodiment the flow diverter 60 is anchored to the LLR with a clip-like anchor 62, to which the diverter 60 is attached.

Figure 6:
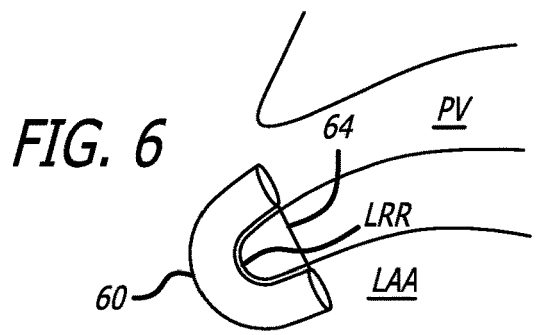
FIG. 6 is a cutaway view of the heart with an embodiment of a shunt placed in the heart according to the invention.

FIG. 6 shows the flow diverter 60 anchored to the LLR with a suture 64. The suture 64 is connected to either end of the diverter 60 and passes through the LLR.

Figure 7:
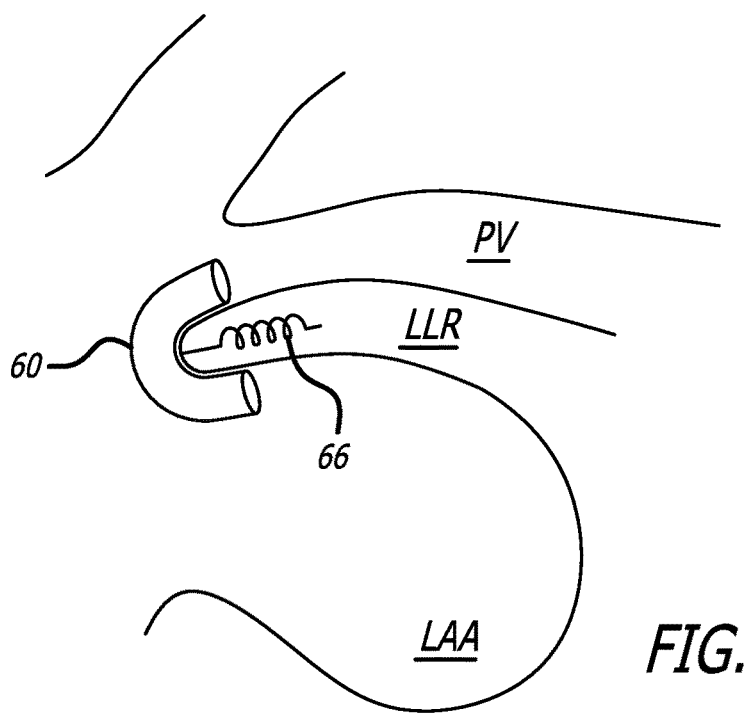
FIG. 7 is a cutaway view of the heart with an embodiment of a shunt placed in the heart according to the invention.

FIG. 7 shows the flow diverter 60 anchored to the LLR with a tissue anchor 66 that is driven into the LLR. The tissue anchor may incorporate a helical tissue screw, such as is shown, or alternative anchor designs utilizing barbs, hooks, memory metal, pedals, arms, and the like, just to name a few non-limiting examples.

Flow diverter 60 does redirect blood flow through a tissue wall, unlike the other embodiments already described herein. As such, it is not important that a fluid-tight passage is provided in a path around the LLR. It is thus envisioned that incomplete flow diverters, such as surfaces rather than tubular stents, may be used to deflect blood flow from the PV into the LAA.

Figure 8:
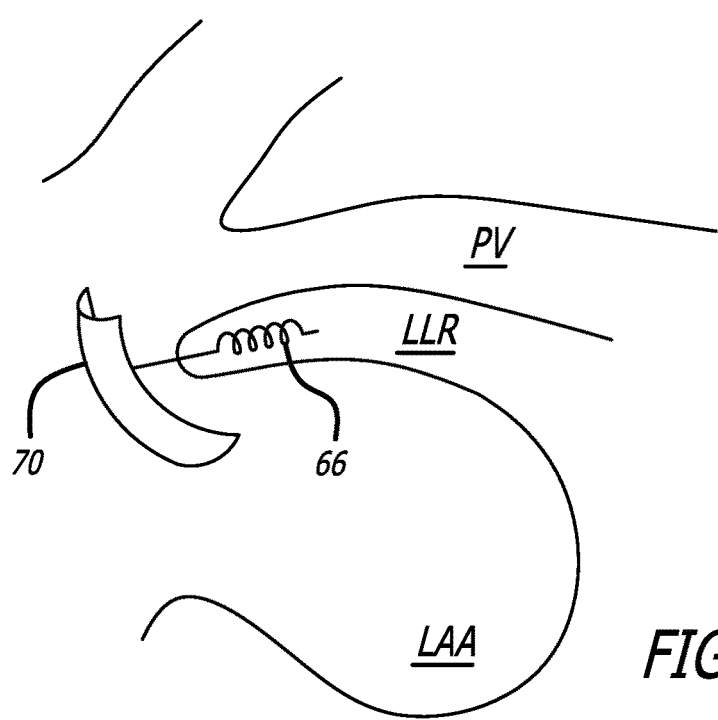
FIG. 8 is a cutaway view of the heart with an embodiment of a flow diverter placed in the heart according to the invention.

FIG. 8 shows one such embodiment of a flow diverter 70 in the form of a ramp. The ramp is a curved surface, rather than a tube, that is anchored to the LRR.

Figure 9:
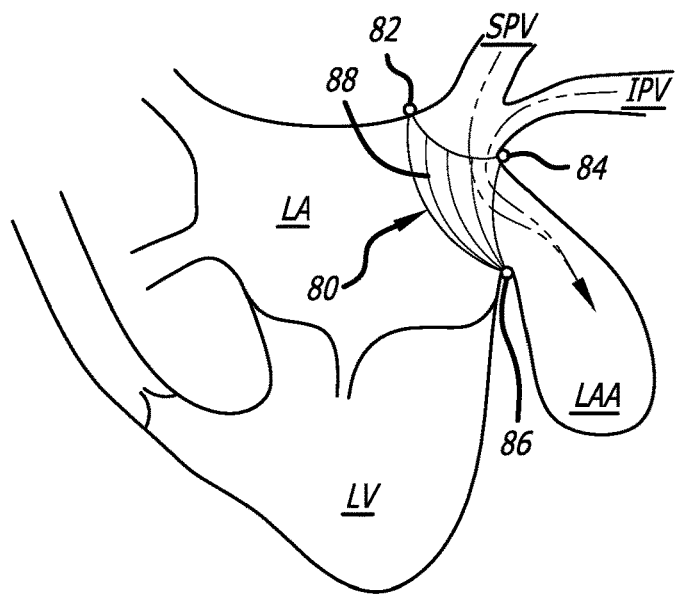
FIG. 9 is a cutaway view of the heart with an embodiment of a flow diverter placed in the heart according to the invention.

FIG. 9 shows another embodiment of a flow diverter 80 in the form of a sail. The sail 80 is a flexible sheet of a material such as fabric, ePTFE, polymer, tissue, to name a few non-limiting examples. The sail is attached to the heart structure at multiple anchor points 82, 84 and 86. Anchor point 82 may be located at the upper side of the ostium of the superior pulmonary vein SPV. Anchor point 84 may be located at the LLR. And anchor point 86 may be located at the lower side of the ostium of the LAA. Additional or alternative anchoring points may also be utilized and placed in locations such as the interatrial septum. The sail 80 may alternatively be placed to bisect the atrium with anchors located at the annulus and at the top of the atrium. Alternatively, the sail 80 could have anchors placed at the annulus, with a shaped wire element used to achieve the angle of the device to redirect flow towards the LAA ostium. Additionally, the sail 80 could employ a suture tightening mechanism to control the amount of blood that is diverted into the LAA. The sail 80 is shown having a plurality of slits that allows some of the blood to flow through the sail 80 into the LA. These slits may increase in width toward the bottom of the LAA ostium such that blood flow is not overly inhibited out of the LAA.

Figure 10:
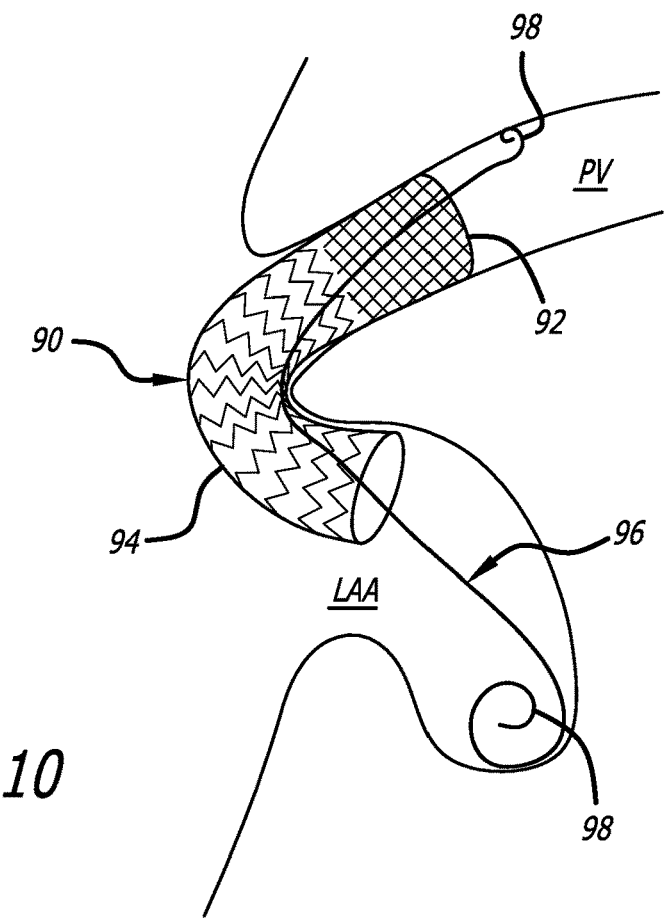
FIG. 10 is a cutaway view of the heart with an embodiment of a shunt placed in the heart according to the invention.

FIG. 10 shows an alternative flow diverter 90 that is in the form of a shunt. The shunt 90 differs from the previous shunts described herein as it includes a proximal stent 92 located in the PV. The proximal stent 92 is a self-expanding stent that acts as both a flow diverting component as well as an anchoring component. Distal of the proximal stent 92 is a shunt body 94 that directs flow from the PV into the LAA.

The shunt body 94 may be completely lined or covered such that all of the blood flow from the PV is directed into the LAA. Alternatively, the shunt body 94 may be partially lined or covered such that some of the flow from the PV is directed into the LAA while some of the flow passes through the wall of the shunt body 94 into the LA. In yet another embodiment, the shunt body 94 is unlined, and the braid or other construction of the shunt body is designed to let a desired amount of blood pass through the body and the rest of the blood is directed into the LAA.

In addition to the anchoring provided by the proximal stent 92, one embodiment further includes a stylet 96 that passes through the flow diverter 90 and includes atraumatic curled ends 98. The stylet 96 is a relatively rigid, spring-like device that prevents migration of the flow diverter 90.

Figure 11:
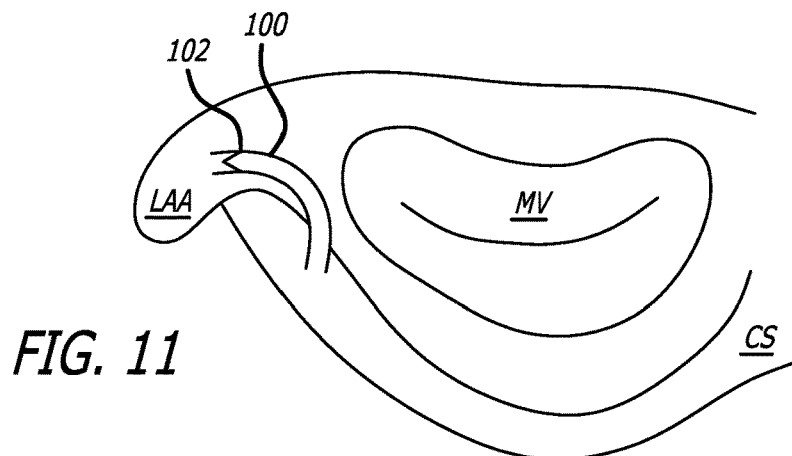
FIG. 11 is a cutaway view of the heart with an embodiment of a shunt placed in the heart according to the invention.

FIG. 11 shows a shunt 100 that is placed between the LAA and the coronary sinus CS to increase flow and reduce stasis. Shunt 100 is shown with an optional valve 102 that ensures blood passes through the valve from the CS to the LAA and not from the LAA to the CS.

Figure 12:
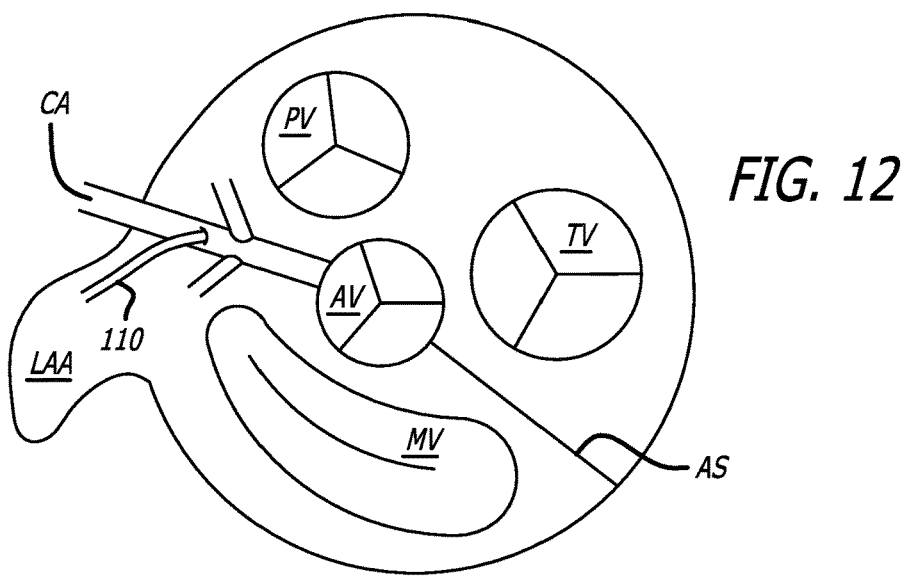
FIG. 12 is a cutaway view of the heart with an embodiment of a shunt placed in the heart according to the invention.

FIG. 12 shows a shunt 110 that is placed between the LAA and the coronary artery CA to increase flow and reduce stasis. Also shown for reference is the pulmonary vein PV, the aortic valve AV, the mitral valve MV, the tricuspid valve TV and the atrial septum AS.

Figure 13:
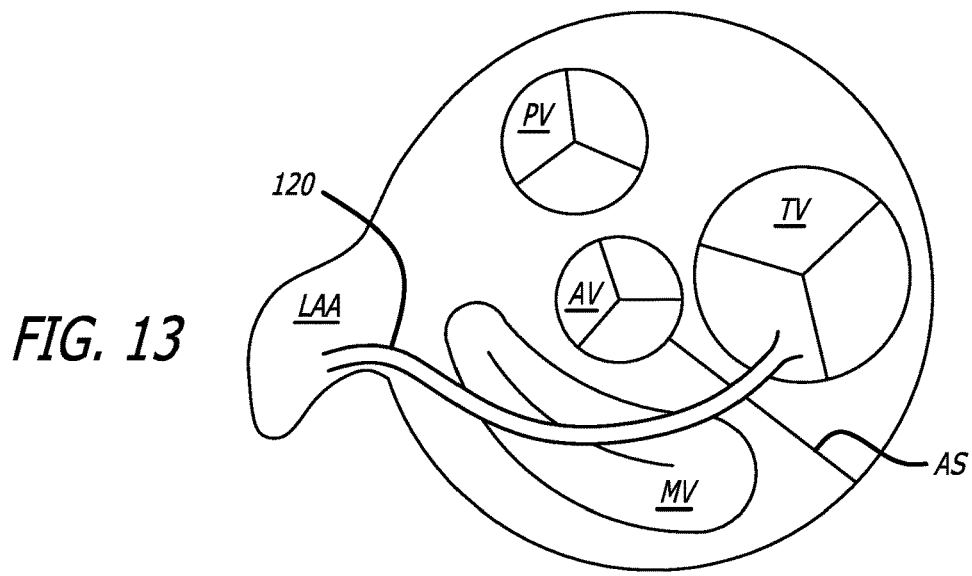
FIG. 13 is a cutaway view of the heart with an embodiment of a shunt placed in the heart according to the invention.

FIG. 13 shows a covered or lined shunt 120 that is placed between the LAA and the RA through the AS to increase flow through the LAA to reduce stasis.

A normally functioning LA reduces stagnation zones by utilizing a vortex-type flow, which is generated by the PV. When a person goes into atrial fibrillation (AFib), flow stagnation occurs on the walls of the LA. This decreases the overall flow velocity.

Figure 14A:
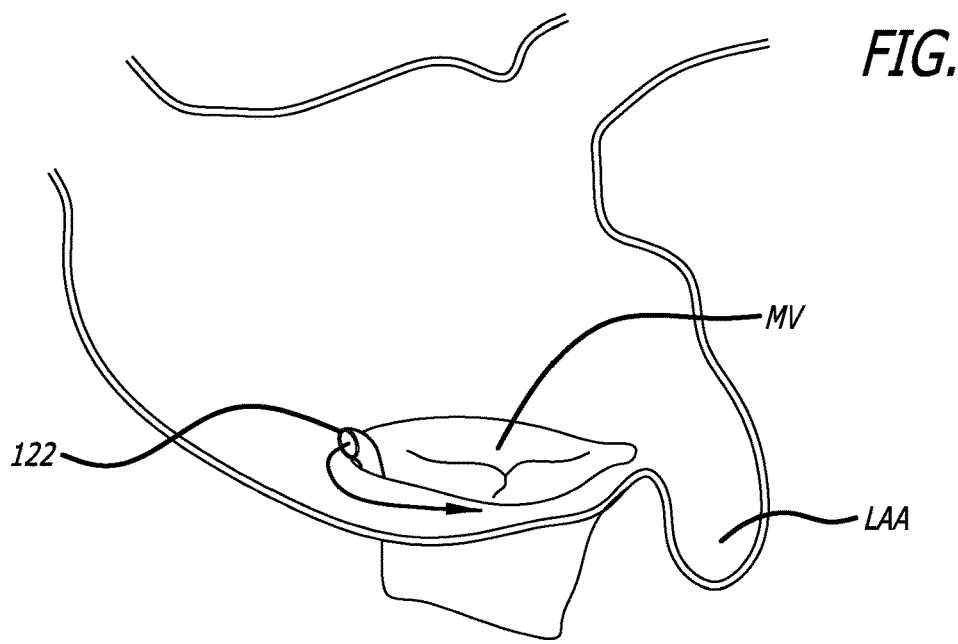
FIG. 14A is a perspective view showing an embodiment of a shunt placed in the MV according to the invention.
Figure 14B:
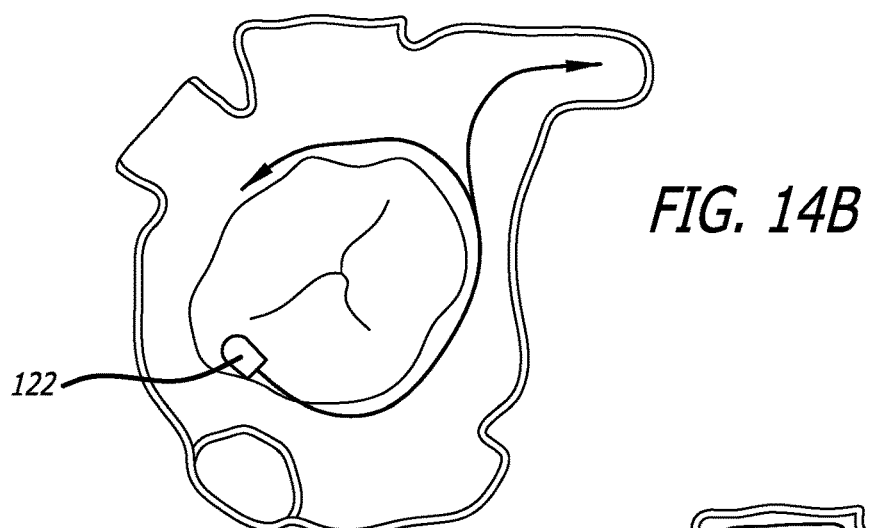
FIG. 14B is a cutaway view of the heart showing the embodiment of FIG. 14A and the flow patterns created thereby.

FIGS. 14A and 14B show an implant 122 that uses a small amount of directed mitral regurgitation to restore normal vortex-type flow in the LA. By restoring vortex flow, stagnation zones are reduced on the walls of the LA during AFib. The implant 122 is easily implanted transseptally in the posterior commissure (or alternatively the anterior commissure) of the MV. The implant 122 could be anchored with barbs or a clip, to name a couple non-limiting examples. Arrows are included that show the resulting flow directions.

Figure 15:
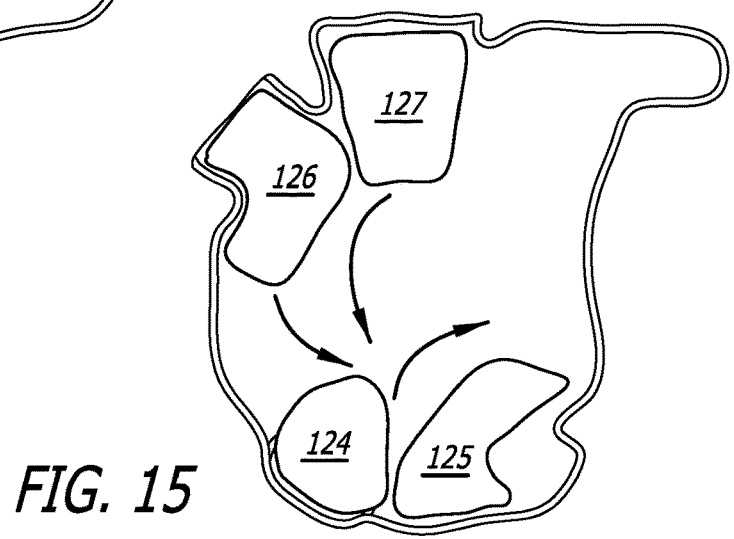
FIG. 15 is a cutaway view of the heart with an embodiment of PV extenders according to the invention.

Another problem that arises during AFib is dilation of the LA, which likely causes flow velocity from the PVs to disperse, reducing vortex formation. This problem is addressed with the flow restoration implants 124, 125, 126 and 127 of FIG. 15. The implants 124, 125, 126 and 127 are conduit extensions for the PVs, and shaped specifically to fit each PV. By extending the conduit of the PVs, the PVs are effectively elongated to compensate for the dilation of the LA, restoring vortex generation and flow augmentation on the LA wall. The PV conduits could be metallic stents to act as platforms for ablation or recurrent ablation for AFib. Arrows are included that show the resulting flow directions.

Figure 16A:
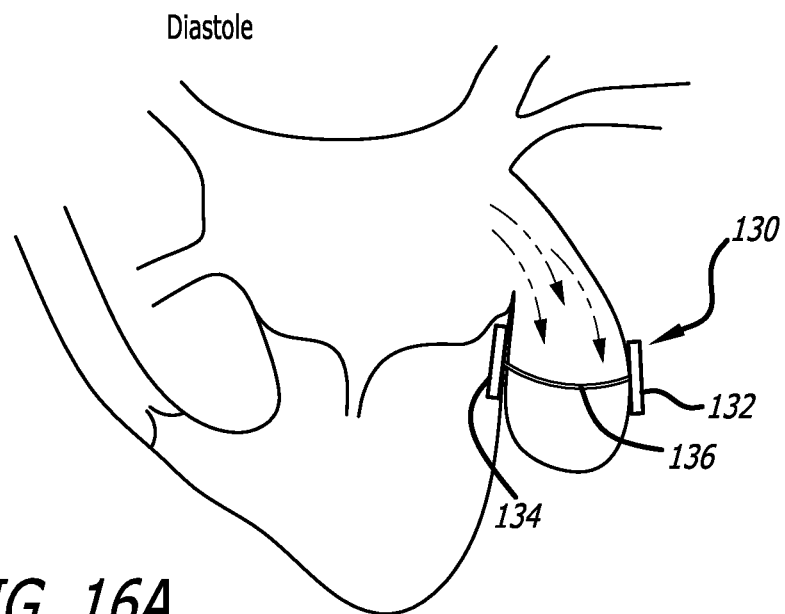
FIG. 16A is a cutaway view of the heart in diastole with an embodiment of a flow generation device placed in the heart according to the invention.
Figure 16B:
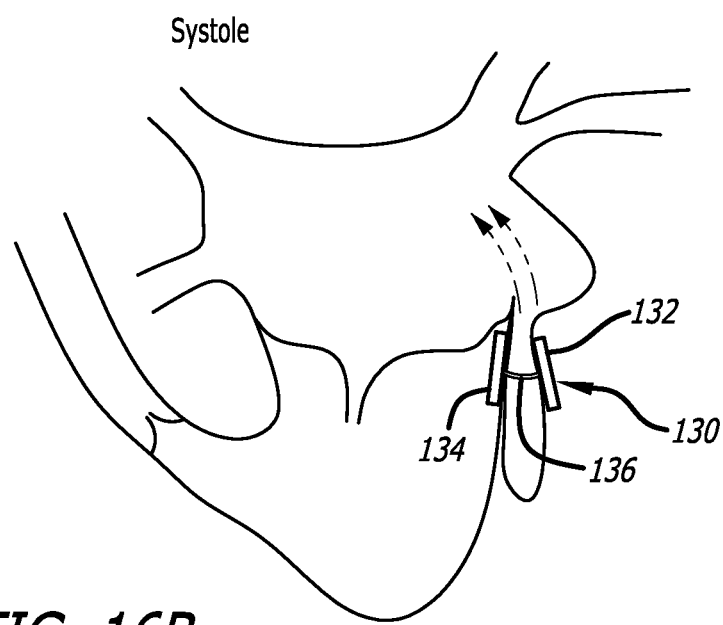
FIG. 16B is a cutaway view of the heart in systole with an embodiment of a flow generation device placed in the heart according to the invention.

FIGS. 16A and 16B show an alternative device 130 for increasing flow through the LAA. The device includes implants that are external to the LAA but use the walls of the LAA to act as a pump. In one example, plates or discs 132 and 134 are placed on opposite sides of the LAA, external to the LAA, and connected through the LAA with a connector 136. In one embodiment, the first plate 132 is placed on an outside surface of the LAA, external to the heart. The second plate 134 is placed in the LV, inside the mitral valve sinus, adjacent the LAA. A driving mechanism, either active or passive, is used to change the distance between the two plates, such that the plates turn the LAA into a bellows that drives blood into and out of the LAA. In the embodiment shown in FIGS. 14A and 14B, the driving mechanism is the heart and the connector 136 has spring properties such that it reacts to the beating heart. FIG. 16A shows the device 130 in a diastole configuration in which the distance between the plates is increased, allowing or drawing blood into the LAA. FIG. 16B shows the device 130 in a systole configuration in which the plates are driven toward each other, collapsing the LAA and forcing the blood out of the LAA into the LA.

Figure 17A:
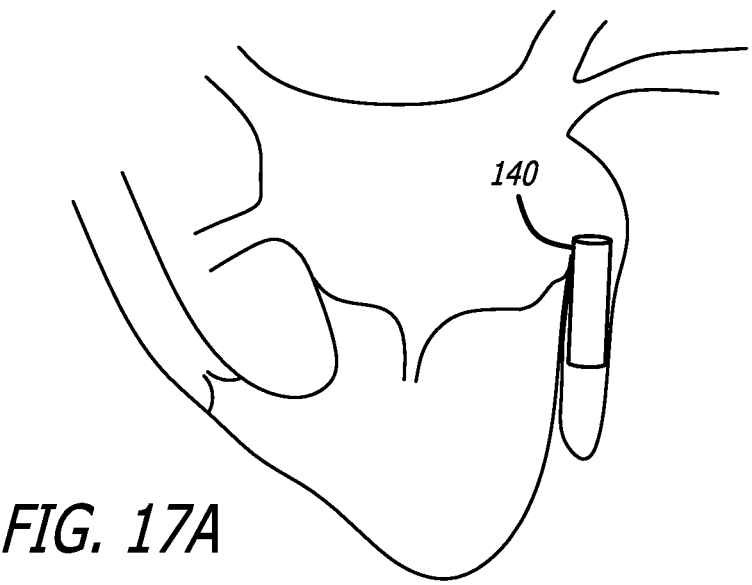
FIG. 17A is a cutaway view of the heart with an embodiment of an unexpanded stent placed in the heart according to the invention.
Figure 17B:
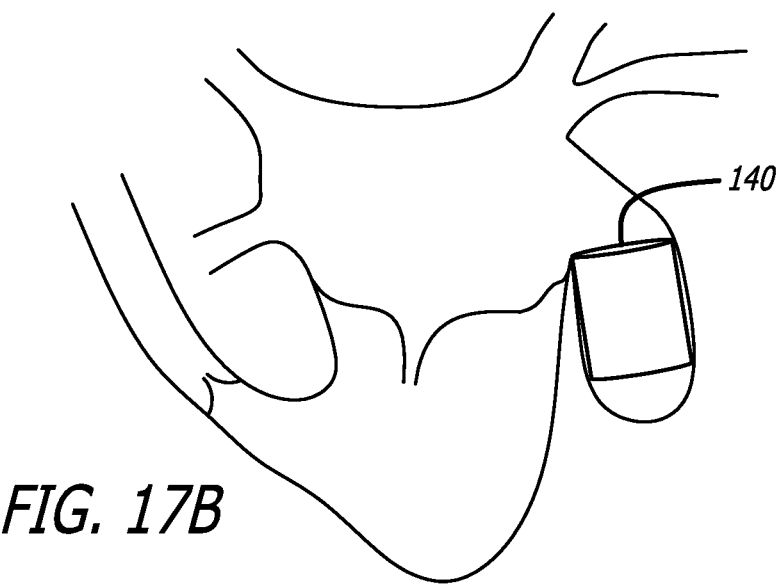
FIG. 17B is a cutaway view of the heart with an embodiment of an expanded stent placed in the heart according to the invention.

FIGS. 17A and 17B show a device 140 that increases flow through the LAA by increasing the size of the LAA cavity as well as the ostium leading to the LAA. The device 140 is a dilating stent that is placed in the LAA and then expanded. The stent 140 may be a self-expanding nitinol braid or a balloon expandable stainless-steel stent structure. One embodiment may include distal barb elements which engage the tissue and may foreshorten the LAA with stent expansion to allow blood to more easily access the apex of the LAA.

FIG. 17A depicts the stent 140 placed in the LAA but not yet expanded. FIG. 17B shows the stent 140 expanded within the LAA. The LAA is wider and shallower in FIG. 17B, as well as having a larger ostium.

Figure 18A:
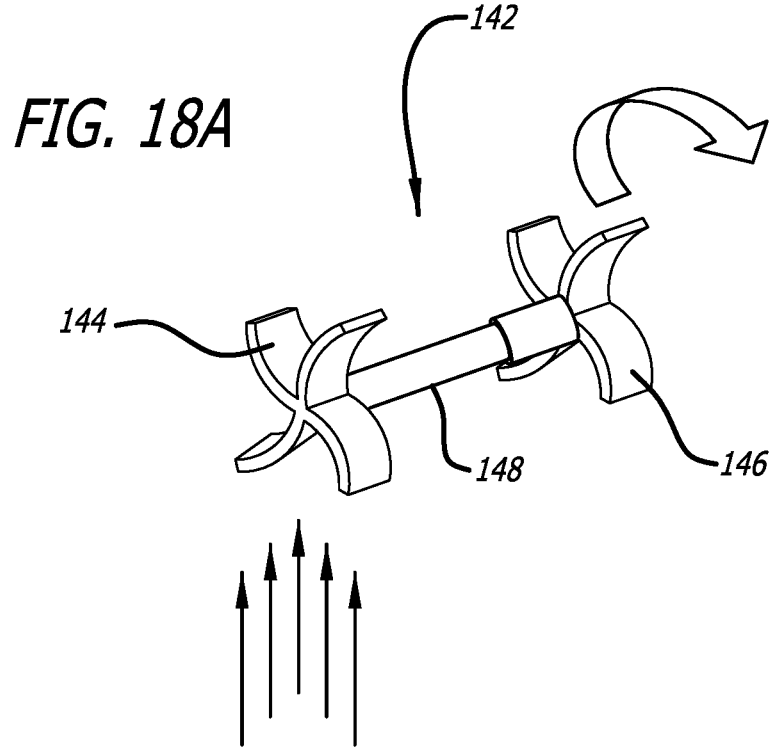
FIG. 18A is an embodiment of an agitation device of the invention.
Figure 18B:
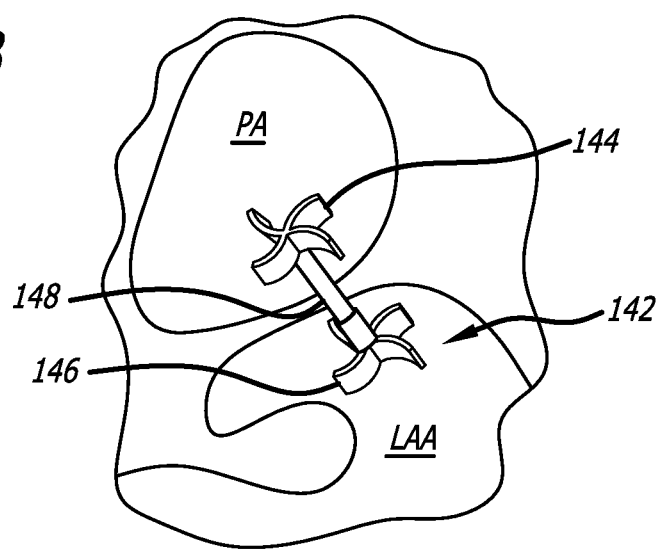
FIG. 18B is a cutaway of the heart with the agitation device of FIG. 18A placed in the heart according to the invention.

FIGS. 18A and 18B show a device 142 that includes a first impeller 144 connected to a second impeller 146 via a shaft 148. The device 142 is implanted between the PA and the LAA such that the first impeller 144 is impacted and rotated by the blood flow through the PA and transfers its rotational energy to the second impeller 146 located in the LAA. The spinning second impeller agitates the blood in the LAA, preventing stasis. In one embodiment the blades of the first and second impellers 144 and 146 are collapsible, such that they may delivered through a catheter. The device 142 is anchored between the PA and the LAA using flanges, fasteners, or any of the other anchoring means described herein or known in the art. The shaft 148 sits in a bushing such that rotation is enabled.

Sealing the LAA

The second category of devices and methods of the invention are directed to reducing flow through the LAA either by reducing the size of the LAA without placing an occlusive device within the LAA, or by blocking the ostium of the LAA.

Figure 19A:
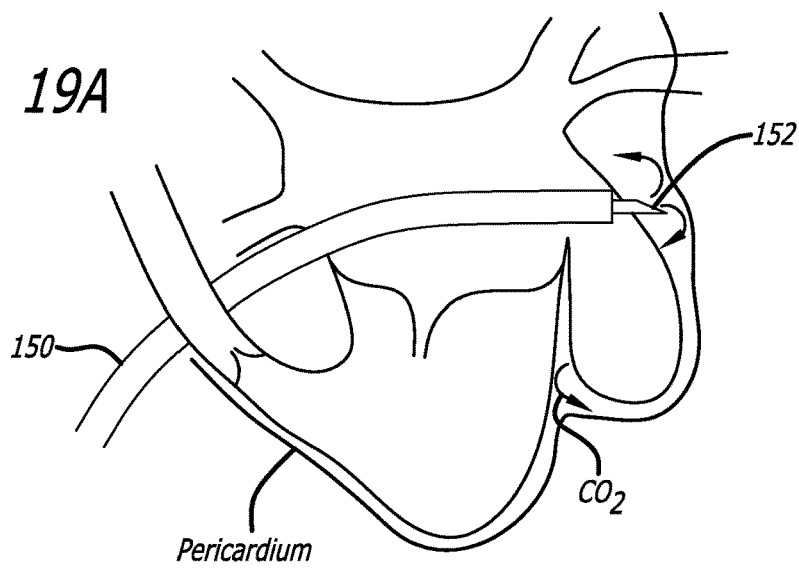
FIG. 19A is a step of an embodiment of invention involving closing the LAA.
Figure 19B:
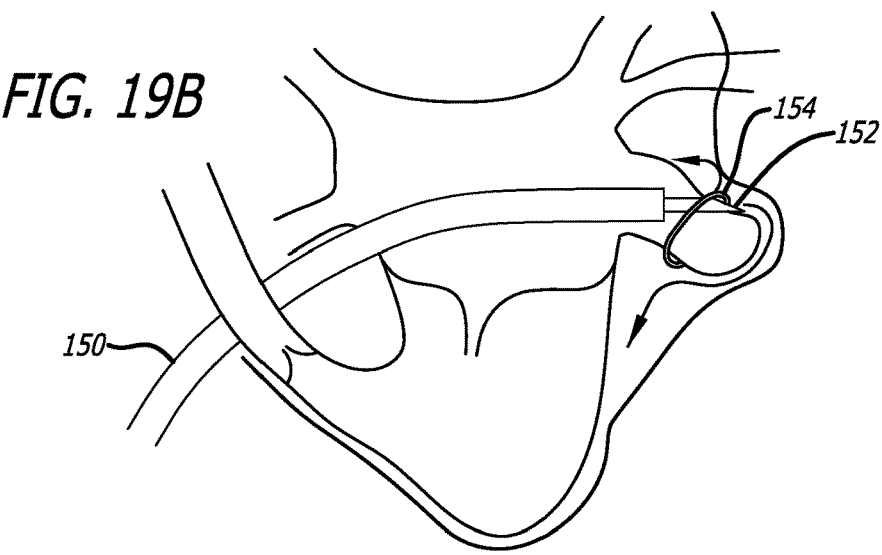
FIG. 19B is a step of an embodiment of invention involving closing the LAA.
Figure 19C:
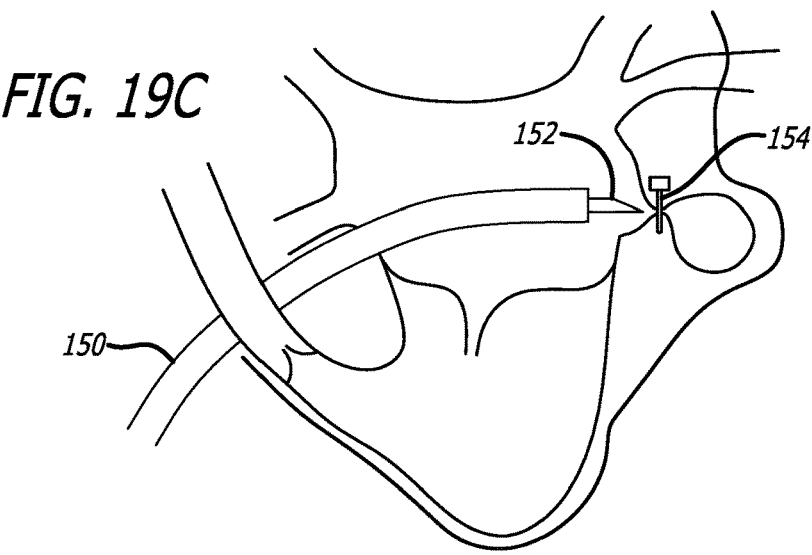
FIG. 19C is a step of an embodiment of invention involving closing the LAA.

Referring to FIGS. 19A-C, there is shown an embodiment that includes a transseptal LAA external cinch closure procedure and device. Referring first to FIG. 19A, a first step is diagrammed that involves navigating a transseptal sheath 150 through the LA and puncturing the wall of the LAA near the upper ostium just below the LLR with a puncture needle 152. CO2 is used to inflate the pericardium such that the LAA becomes spaced-apart from the LV. Other gases or fluids could also be used to create this separation.

In FIG. 19B, a cinch loop 154 is deployed from the puncture needle and placed around the LAA within the pericardial space created by the CO2 insufflation.

In FIG. 19C, the final step is shown in which the cinch loop 154 is tightened and locked in place and the needle 152 and sheath 150 is removed. The method results in a complete collapsing of the LAA ostium and the risk of thrombus forming is eliminated.

Figure 20A:
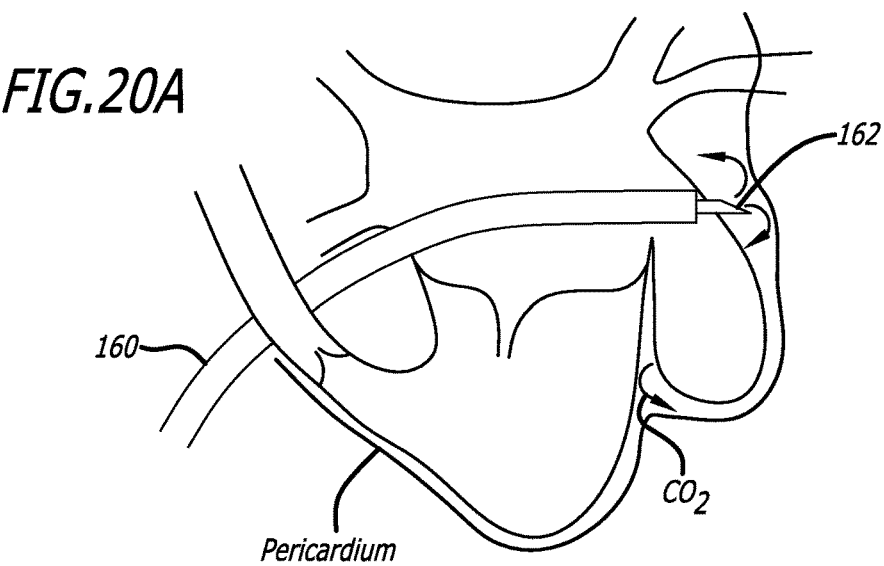
FIG. 20A is a step of an embodiment of invention involving closing the LAA.

An alternative method of closing off the ostium of the LAA is shown in FIGS. 18A-C. Referring first to FIG. 20A, a first step is diagrammed that involves navigating a transseptal sheath 160 through the LA and puncturing the wall of the LAA near the upper ostium just below the LLR with a puncture needle 162. CO2 is used to inflate the pericardium such that the LAA becomes spaced-apart from the LV.

Figure 20B:
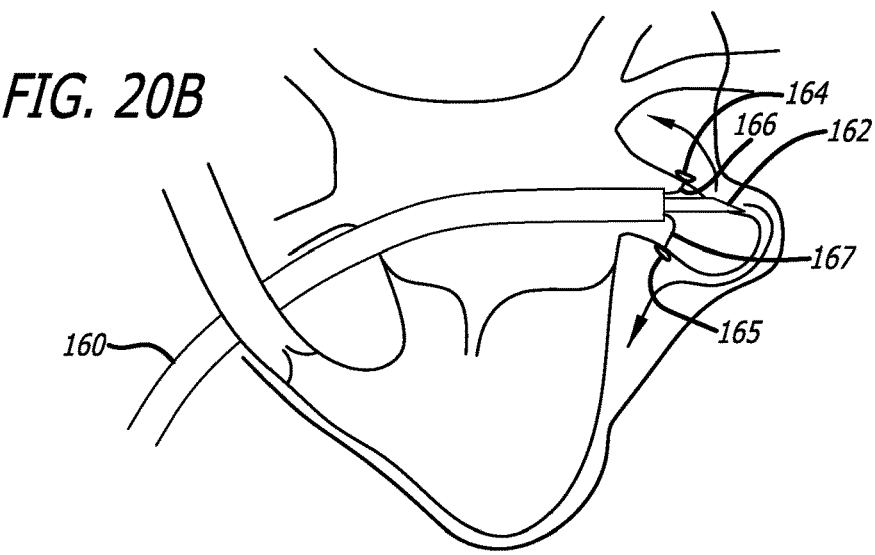
FIG. 20B is a step of an embodiment of invention involving closing the LAA.

In FIG. 20B, pads 164 and 165 are placed on opposite sides of the LAA in the pericardial space and connected to cinch sutures 166 and 167.

Figure 20C:
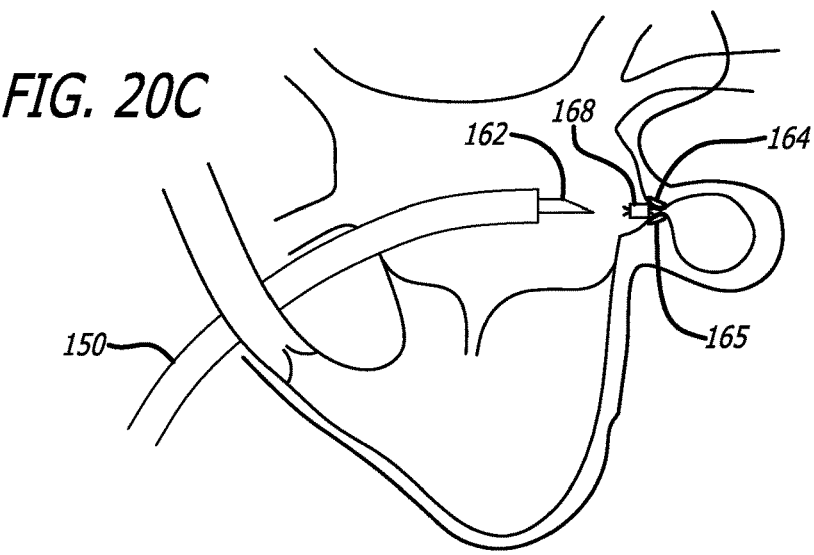
FIG. 20C is a step of an embodiment of invention involving closing the LAA.

In FIG. 20C, the final step is shown in which the cinch sutures 166 and 167 are drawn together, pulling the pads together and closing off the LAA. A lock 168 is then employed around the sutures 166 and 167 to prevent the pads 164 and 165 from separating. The method also results in a complete collapsing of the LAA ostium and the risk of thrombus forming is eliminated.

Figure 21A:
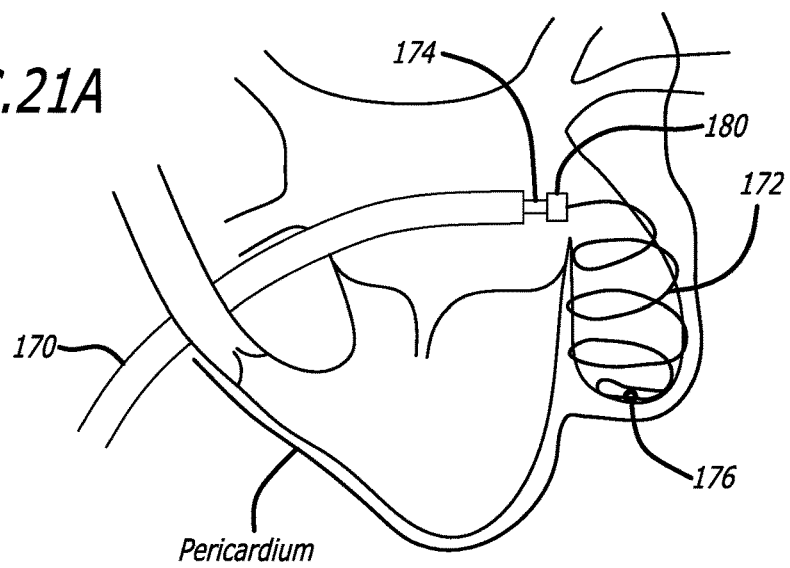
FIG. 21A is a step of an embodiment of invention involving closing the LAA.
Figure 21B:
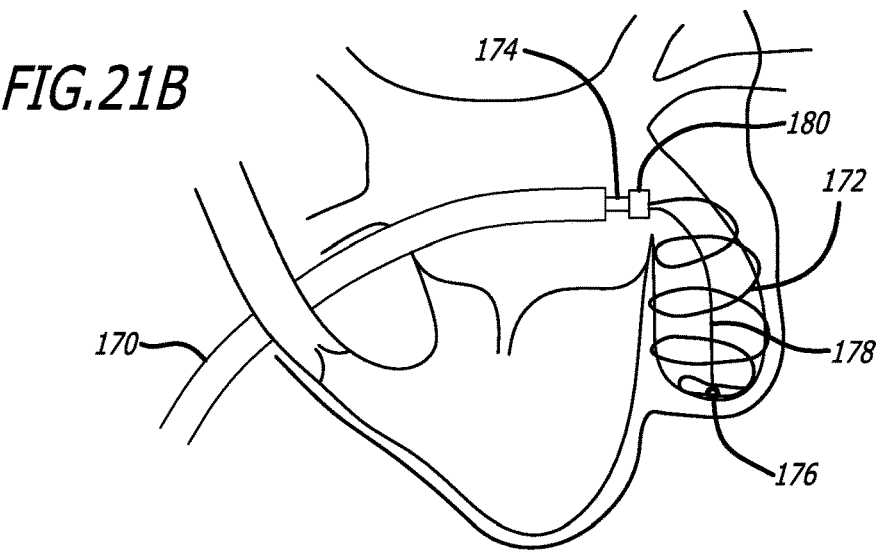
FIG. 21B is a step of an embodiment of invention involving closing the LAA.
Figure 21C:
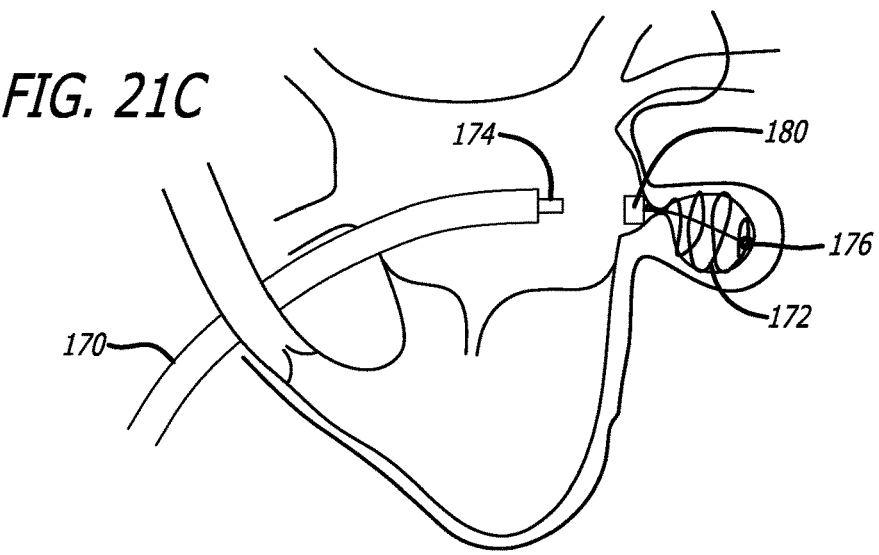
FIG. 21C is a step of an embodiment of invention involving closing the LAA.

FIGS. 21A-C show an embodiment of a method used to close the LAA using a corkscrew-shaped cinch wire. In FIG. 21A a first step is diagrammed that involves navigating a transseptal sheath 170 through the LA and puncturing the wall of the LAA near the upper ostium just below the LLR with a corkscrew wire 172. CO2 or other gases or fluids could be used to inflate the pericardium such that the LAA becomes spaced-apart from the LV. A torque shaft 174 within the sheath 170 is used to rotate the corkscrew wire 172 as it is extended resulting in a surrounding of the LAA. The distal end of the wire 172 includes a cinch feature 176 that is used for retrieval and for transferring force to the LAA during cinching.

FIG. 21B shows the cinch feature 176 being retrieved by a cinch wire 178 that is advanced from the torque shaft 174 through a releasable lock nut 180 positioned at the distal end of the torque shaft 174.

In FIG. 21C, the cinch feature 176 is pulled toward the lock nut with the cinch wire 178 while the corkscrew wire 172 is simultaneously retracted. Once the two wires 172 and 178 are retracted and the LAA is closed, the lock nut 180 is released and prevents the wires from loosening. The excess wire could then be cut and removed.

Figure 22A:
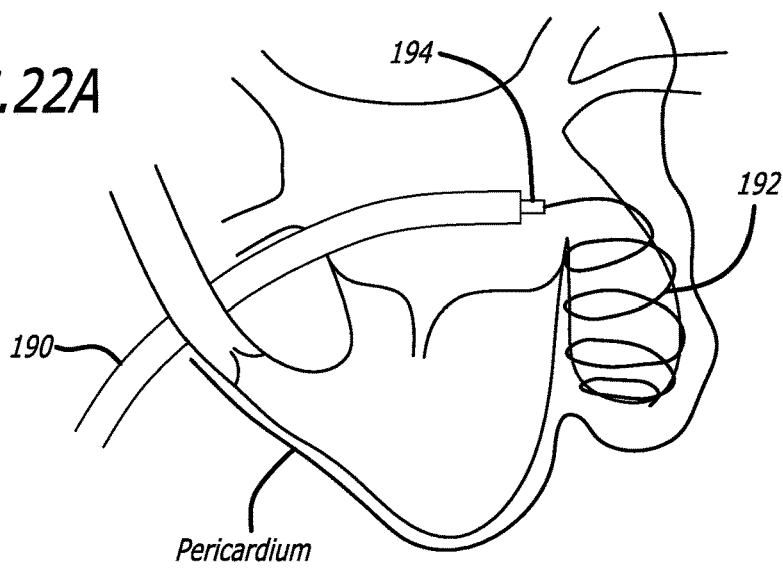
FIG. 22A is a step of an embodiment of invention involving closing the LAA.
Figure 22B:
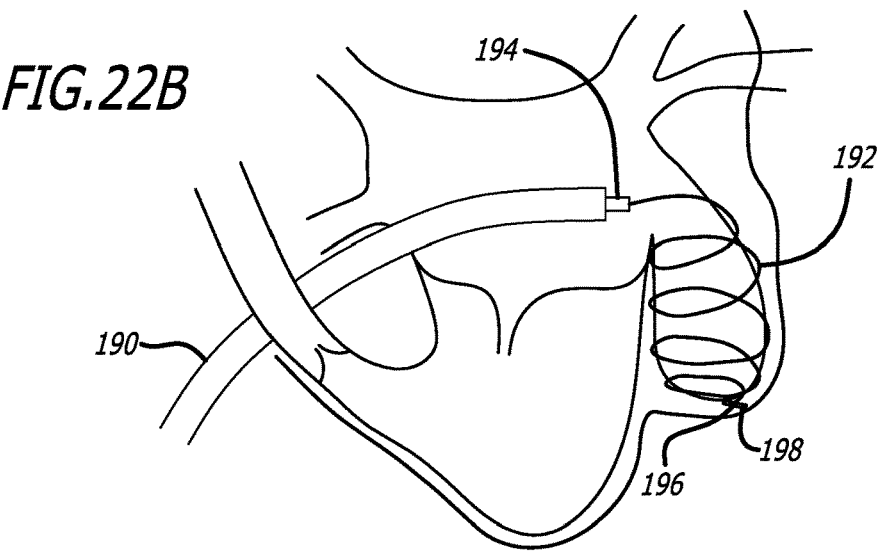
FIG. 22B is a step of an embodiment of invention involving closing the LAA.
Figure 22C:
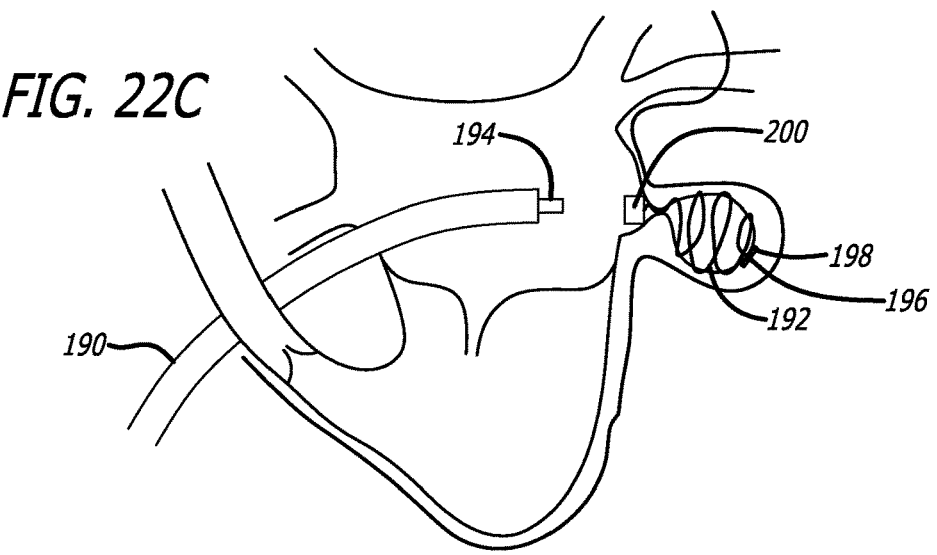
FIG. 22C is a step of an embodiment of invention involving closing the LAA; and, FIG. 23 is a cutaway view of the heart with an embodiment of a flow diverter placed in the heart according to the invention.

FIGS. 22A-C show an embodiment of a method used to close the LAA using a helical needle to wrap a suture around the LAA. In FIG. 22A a first step is diagrammed that involves navigating a transseptal sheath 190 through the LA and puncturing the wall of the LAA near the upper ostium just below the LLR with a hollow spiral needle 192. CO2 is used to inflate the pericardium such that the LAA becomes spaced-apart from the LV. CO2 could again be used for this purpose. A torque shaft 194 within the sheath 190 is used to rotate the needle 192 as it is extended resulting in a surrounding of the LAA.

In FIG. 22B, a suture rod is advanced through the needle with a suture 196 attached to the end of the rod. A suture knot 198 is used to attach the distal end of the suture 196 to the outside of the LAA.

In FIG. 22C, the suture rod and needle are retracted leaving the suture helically surrounding the LAA. The suture 196 is then cinched and a lock clip 200 is used to maintain the suture in a cinched configuration around the LAA. The excess suture is cut and removed.

Figure 23:
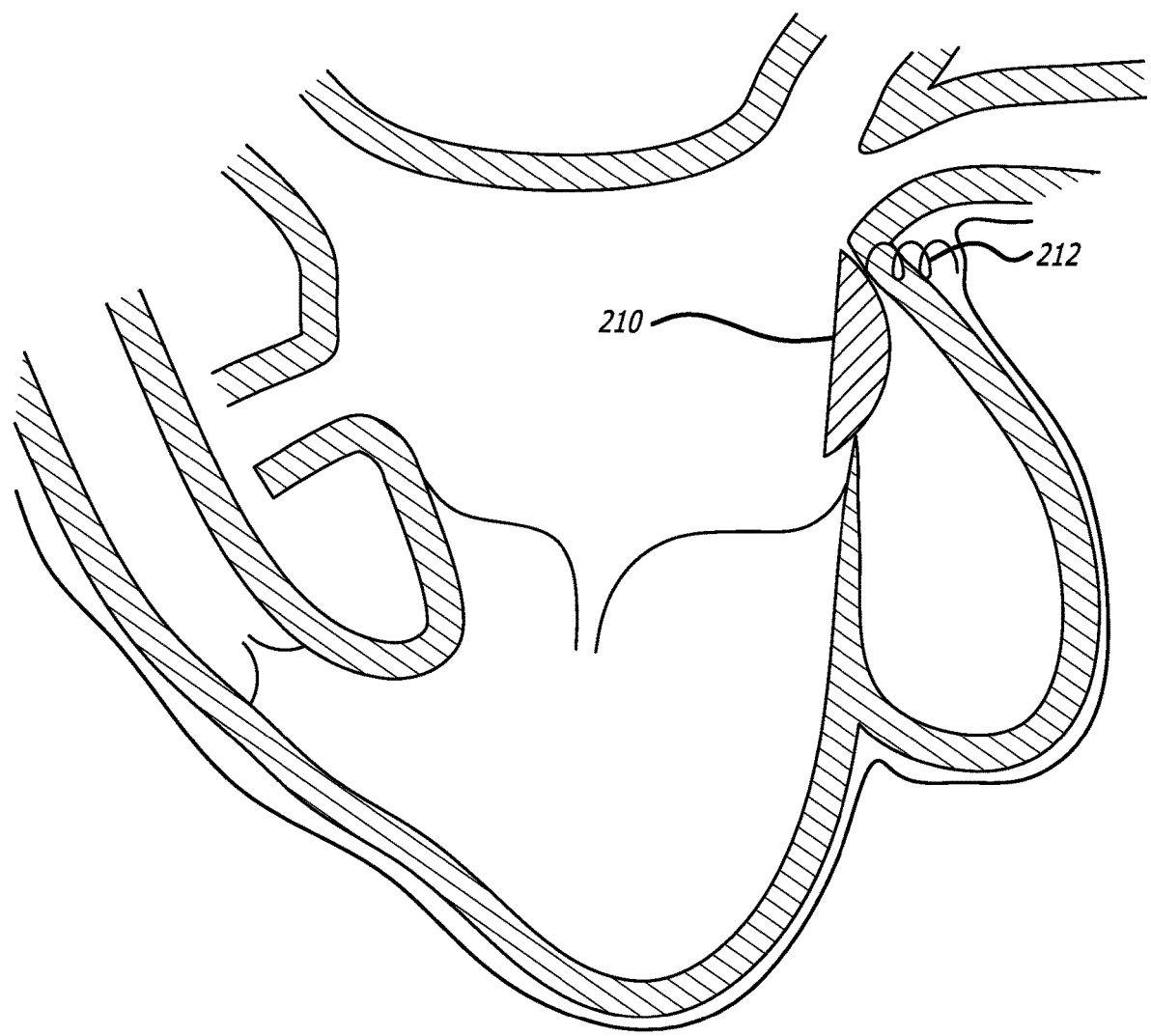

FIG. 23 depicts an embodiment of a closure device 210 that is positioned with anchor 212 to the LLR and contains a conforming structure to occlude the LAA ostium. The device 210 may contain a torsional element to apply force to the occlusive element to provide a better seal. The device could be anchored at the LLR which forms a stable and consistent anchoring point outside the ostium. External anchoring and sealing of the ostium could address some of the limitations of the occlusion devices currently on the market.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of increasing flow through a left atrial appendage comprising:
   creating a passageway traversing through a wall of a pulmonary vein and a wall of the left atrial appendage; and
   actively diverting flow from the pulmonary vein directly into the left atrial appendage through the passageway such that the flow passes into the left atrial appendage and washes out the left atrial appendage.

2. The method of claim 1, wherein creating the passageway traversing through the wall of the pulmonary vein and the wall of the left atrial appendage comprises placing a flow diverter in the pulmonary vein that leads directly into the left atrial appendage.

3. The method of claim 2, wherein the flow diverter is positioned upstream of a left lateral ridge.

4. The method of claim 1, wherein the actively diverting flow step is comprised of diverting a majority of the flow from the pulmonary vein directly into the left atrial appendage.

5. The method of claim 1, further comprising implanting a flow resistor downstream of the passageway.

6. The method of claim 5, wherein the flow resistor is implanted near a left lateral ridge.

7. The method of claim 1, wherein the actively diverting flow step is comprised of resistively diverting flow from the pulmonary vein directly into the left atrial appendage.

8. A method of increasing a blood flow through a left atrial appendage, comprising:
 connecting an inlet of a flow diverter to a pulmonary vein such that the inlet of the flow diverter extends through a wall of the pulmonary vein;
 connecting an outlet of the flow diverter to the left atrial appendage such that the outlet of the flow diverter extends through a wall of the left atrial appendage, wherein the flow diverter is placed directly between the pulmonary vein and the left atrial appendage; and
 actively diverting at least a portion of the blood flow through the flow diverter into the left atrial appendage to wash out the left atrial appendage.

9. The method of claim 8, further comprising causing a majority of the blood flow to flow through the inlet of the flow diverter.

10. The method of claim 8, further comprising implanting a flow resistor downstream of the flow diverter.

11. The method of claim 10, wherein the flow resistor is separate from the flow diverter.

12. The method of claim 10, wherein the flow resistor is placed near a left lateral ridge.

13. The method of claim 10, wherein the flow resistor is comprised of a stent.

14. The method of claim 10, wherein the flow resistor is comprised of a braided flow inhibitor.

15. The method of claim 8, further comprising orienting the outlet of the flow diverter towards a sidewall of the left atrial appendage such that the blood flow creates a vortex within the left atrial appendage.

16. A method of increasing a blood flow through a left atrial appendage, comprising:
 penetrating through a wall of a pulmonary vein;
 penetrating through a wall of a left atrial appendage;
 creating a passageway traversing through the wall of the pulmonary vein and the wall of the left atrial appendage;
 wherein an inlet of the passageway extends through the wall of the pulmonary vein;
 wherein an outlet of the passageway extends through the wall of the left atrial appendage; and
 actively diverting at least a portion of the blood flow from the pulmonary vein directly into the left atrial appendage through the passageway such that the at least a portion of the blood flow passes into the left atrial appendage and washes out the left atrial appendage.

17. The method of claim 16, further comprising placing a flow resistor in the pulmonary vein downstream of the passageway.

18. The method of claim 16, further comprising causing a majority of the blood flow to flow through the inlet of the passageway.

* * * * *